US009510594B2

(12) United States Patent
Görtz et al.

(10) Patent No.: US 9,510,594 B2
(45) Date of Patent: Dec. 6, 2016

(54) USE OF SDHI FUNGICIDES ON CONVENTIONALLY BRED ASR-TOLERANT, STEM CANKER RESISTANT AND/OR FROG-EYE LEAF SPOT RESISTANT SOYBEAN VARIETIES

(75) Inventors: Andreas Görtz, Dormagen (DE); Heiko Rieck, Burscheid (DE); Hiroyuki Hadano, Tochigi (JP)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 398 days.

(21) Appl. No.: 13/984,654

(22) PCT Filed: Feb. 13, 2012

(86) PCT No.: PCT/EP2012/052430
§ 371 (c)(1),
(2), (4) Date: Oct. 22, 2013

(87) PCT Pub. No.: WO2012/110464
PCT Pub. Date: Aug. 23, 2012

(65) Prior Publication Data
US 2014/0039027 A1 Feb. 6, 2014

Related U.S. Application Data

(60) Provisional application No. 61/443,849, filed on Feb. 17, 2011.

(30) Foreign Application Priority Data

Feb. 17, 2011 (EP) .................................. 11154827

(51) Int. Cl.
| | |
|---|---|
| *A61K 31/415* | (2006.01) |
| *C07D 231/00* | (2006.01) |
| *A01H 5/00* | (2006.01) |
| *A01N 43/56* | (2006.01) |
| *A01H 5/10* | (2006.01) |
| *A01N 25/00* | (2006.01) |
| *A01N 65/00* | (2009.01) |

(52) U.S. Cl.
CPC ............... *A01N 43/56* (2013.01); *A01H 5/10* (2013.01); *A01N 25/00* (2013.01); *A01N 65/00* (2013.01)

(58) Field of Classification Search
None
See application file for complete search history.

(56) References Cited

U.S. PATENT DOCUMENTS

| | | | |
|---|---|---|---|
| 5,747,518 A | 5/1998 | Yoshikawa et al. | |
| 6,936,752 B1 * | 8/2005 | Streit et al. | 800/312 |
| 7,335,661 B2 * | 2/2008 | Tormo i Blasco et al. | 514/259.31 |
| 7,459,477 B2 | 12/2008 | Furuya et al. | |
| 7,521,397 B2 | 4/2009 | Dunkel et al. | |
| 7,538,073 B2 | 5/2009 | Elbe et al. | |
| 7,563,921 B2 | 7/2009 | von Deyn et al. | |
| 7,572,818 B2 | 8/2009 | Mansfield et al. | |
| 7,872,036 B2 | 1/2011 | Toriyabe et al. | |
| 7,897,630 B2 | 3/2011 | Lahm et al. | |
| 7,951,752 B2 | 5/2011 | Ehrenfreund et al. | |
| 8,084,452 B2 | 12/2011 | Jeschke et al. | |
| 8,106,212 B2 | 1/2012 | Jeschke et al. | |
| 8,129,526 B2 | 3/2012 | Mizuno et al. | |
| 8,138,350 B2 | 3/2012 | Jeschke et al. | |
| 8,153,560 B2 | 4/2012 | Langewald et al. | |
| 8,198,215 B2 | 6/2012 | Walter et al. | |
| 8,202,890 B2 | 6/2012 | Goto et al. | |
| 8,324,390 B2 | 12/2012 | Fischer et al. | |
| 8,362,046 B2 | 1/2013 | Huang et al. | |
| 8,404,855 B2 | 3/2013 | Jeschke et al. | |
| 8,415,369 B2 | 4/2013 | Zambach et al. | |
| 8,470,856 B2 | 6/2013 | Koyanagi et al. | |
| 8,492,311 B2 | 7/2013 | Mita et al. | |
| 8,507,532 B2 | 8/2013 | Qin et al. | |
| 2007/0071782 A1 | 3/2007 | Deyn et al. | |
| 2008/0069930 A1 | 3/2008 | Wood et al. | |
| 2008/0070785 A1 | 3/2008 | Walter et al. | |
| 2008/0108686 A1 | 5/2008 | Gewehr et al. | |
| 2009/0069317 A1 | 3/2009 | Pohlman et al. | |
| 2009/0111847 A1 | 4/2009 | Li et al. | |
| 2009/0124498 A1 | 5/2009 | von Deyn et al. | |
| 2010/0093715 A1 | 4/2010 | Voeste et al. | |

(Continued)

FOREIGN PATENT DOCUMENTS

| | | | |
|---|---|---|---|
| EP | 0539588 A1 | 5/1993 | |
| EP | 0737682 B1 | 10/1996 | |

(Continued)

OTHER PUBLICATIONS

Godoy, Changes in performance of SBR fungicides over the years and new management strategies adopted in Brazil, National Soybean Rust Symposium, 2009.*
Ribeiro et al., Genetic control of Asian rust in soybean, Euphytica, 157:15-25, 2007.*
Magalhaes, et al. "Brazil Launches Rust Resistant Soybean: Inox Available for Upcoming Planting Season", DTN/The Progressive Farmer, Jul. 2009, 09:09.

(Continued)

*Primary Examiner* — Jeffrey S Lundgren
*Assistant Examiner* — Michael Schmitt
(74) *Attorney, Agent, or Firm* — McBee Moore Woodward Vanik IP LLC

(57) ABSTRACT

The present invention relates to a method for controlling Asian soybean rust (ASR) of a conventionally bred ASR-tolerant, Stem canker resistant and/or Frog-eye leaf spot resistant soybean variety comprising the application of a succinate dehydrogenase inhibitor (SDHI) fungicide to said plant, plant propagation material, or at its locus of growth.

21 Claims, No Drawings

(56) References Cited

U.S. PATENT DOCUMENTS

| | | |
|---|---|---|
| 2010/0168177 A1 | 7/2010 | Qin et al. |
| 2011/0112124 A1 | 5/2011 | Haas et al. |
| 2011/0203018 A1 | 8/2011 | Gewehr et al. |
| 2011/0209253 A1 | 8/2011 | Grossmann et al. |
| 2011/0212949 A1 | 9/2011 | Bretschneider et al. |
| 2011/0306499 A1 | 12/2011 | Bretschneider et al. |

FOREIGN PATENT DOCUMENTS

| | | | |
|---|---|---|---|
| JP | 2008110953 A | 11/2009 | |
| JP | 2010018586 A | 10/2011 | |
| WO | 02096882 A1 | 12/2002 | |
| WO | 03010149 A1 | 2/2003 | |
| WO | 03070705 A1 | 8/2003 | |
| WO | 03074491 A1 | 9/2003 | |
| WO | 2004016088 A2 | 2/2004 | |
| WO | 2004099160 A1 | 11/2004 | |
| WO | 2005035486 A1 | 4/2005 | |
| WO | 2005063094 A1 | 7/2005 | |
| WO | 2005077934 A1 | 8/2005 | |
| WO | 2005085216 A1 | 9/2005 | |
| WO | 2005123690 A1 | 12/2005 | |
| WO | 2006015865 A1 | 2/2006 | |
| WO | 2006015866 A1 | 2/2006 | |
| WO | 2006043635 A1 | 4/2006 | |
| WO | 2006056433 A2 | 6/2006 | |
| WO | 2006056433 A3 | 6/2006 | |
| WO | 2006100288 A2 | 9/2006 | |
| WO | 2007057407 A2 | 5/2007 | |
| WO | 2007075459 A2 | 7/2007 | |
| WO | 2007101369 A1 | 9/2007 | |
| WO | 2007115643 A1 | 10/2007 | |
| WO | 2007115644 A1 | 10/2007 | |
| WO | 2007115646 A1 | 10/2007 | |
| WO | 2007149134 A1 | 12/2007 | |
| WO | 2008009360 A2 | 1/2008 | |
| WO | WO 2008/049575 A2 * | 5/2008 | ............. A01N 37/50 |
| WO | WO2008/049575 A2 * | 5/2008 | ............. A01N 37/50 |
| WO | 2008066153 A1 | 6/2008 | |
| WO | 2008067911 A1 | 6/2008 | |
| WO | 2008104503 A1 | 9/2008 | |
| WO | 2009049851 A1 | 4/2009 | |
| WO | 2010000612 A1 | 1/2010 | |
| WO | 2010006713 A1 | 1/2010 | |
| WO | 2010006713 A2 | 1/2010 | |
| WO | 2010006713 A3 | 1/2010 | |
| WO | 2010046380 A2 | 4/2010 | |
| WO | 2010046380 A3 | 4/2010 | |
| WO | 2010049405 A1 | 5/2010 | |
| WO | 2010069502 A2 | 6/2010 | |
| WO | 2010069502 A8 | 6/2010 | |
| WO | 2010074747 A8 | 7/2010 | |
| WO | 2010074751 | 7/2010 | |
| WO | 2010096227 A1 | 8/2010 | |

OTHER PUBLICATIONS

International Search Report for PCT/EP2012/052430 Mailed Jul. 3, 2012.

* cited by examiner

USE OF SDHI FUNGICIDES ON CONVENTIONALLY BRED ASR-TOLERANT, STEM CANKER RESISTANT AND/OR FROG-EYE LEAF SPOT RESISTANT SOYBEAN VARIETIES

CROSS REFERENCE TO RELATED APPLICATIONS

This application is a §371 National Stage Application of PCT/EP2012/052430, filed Feb. 13, 2012, which claims priority to European Application No. 11154827.7, filed Feb. 17, 2011, and U.S. Provisional Application No. 61/443,849, filed Feb. 17, 2011.

BACKGROUND OF THE INVENTION

1. Field of the Invention

The present invention relates to a method for controlling Asian soybean rust (ASR) of a conventionally bred ASR-tolerant, Stem canker resistant and/or Frog-eye leaf spot resistant soybean variety comprising the application of a succinate dehydrogenase inhibitor (SDHI) fungicide to said plant, plant propagation material, or at its locus of growth.

2. Description of Related Art

Soybean (genus *Glycine*) is considered to be an important crop and is highly valued by world agriculture. Therefore, one of the major objectives of the soybean breeders is to develop more stable, productive and disease-resistant varieties. The basic motivation is to maximize grain yield for human and animal consumption. In order to attain said objects, the breeder usually selects varieties having superior traits.

Asian soybean rust (ASR), caused by the fungus *Phakopsora pachyrhizi*, is considered to be the most destructive soybean leaf disease (Miles, M. R.; Frederick R. D.; Hartman, G. (2003) Soybean rust: Is the U. S. soybean crop at risk? Online. APSnet Feature, American Phytopathological Society). The disease spreads by windblown uredospores which consequently let to long-distance dispersal to new, rust-free regions. Therefore, ASR has already caused losses in many soybean-growing regions of the world. The impact of the pathogen on productivity is drastic: up to 80% yield loss was observed in some regions (Yorinori J. T. (2004) Ferrugem "asiática" da soja no Brasil: evoluçõ, importáncia econômica e controle. In: Junior J. N. Lazzarotto J. J. (eds.) Documentos 247. Embrapa, Londrina, Brazil, 36).

In order to control the disease, fungicides are applied or resistant or tolerant varieties are used.

The application of fungicides commonly bears the problem of unfavorable environmental or toxicological effects due to high dosage rates which are needed to effectively control the disease.

Fungus resistance is known to naturally occur in genotypes of the *Glycine* genus (Burdon, J. J.; Marshall, D. R. (1981) Evaluation of Australian native species of *Glycine canescens*, a wild relative of soybean. Theoretical Applied Genetics, 65: 44-45; Burdon, J. J. (1988) Major gene resistance to *Phakopsora pachyrhizi* in *Glycine canescens*, a wild relative of soybean. Theoretical Applied Genetics, 75: 923-928). Five qualitative dominant resistance genes have been identified (Meyer J. D. F., et al., (2009) Identification and analyses of candidate genes for rpp4-mediated resistance to ASR in soybean, Plant Physiology, 150: 295-307; Oloka H. K.; Tukamuhabwa P. (2008) Reaction of exotic soybean germplasm to *Phakopsora pachyrhizi* in Uganda, Plant Disease, 92: 1493-1496): rpp 1 in PI200492 (McLean, R. J.; Byth, D. E. (1980) Inheritance of resistance to rust (*Phakopsora pachyrhizi*) in soybean. Australian Journal Agricultural research, 31: 951-956); rpp2 in PI230970 (Bromfield, K. R.; Hartwig E. E. (1980) Resistance to soybean rust and mode of inheritance. Crop Science, 20: 254-255); rpp3 in PI 462312 (Bromfield K. R.; Melching, J. S. (1982) Sources of specific resistance to soybean rust. Phytopathology, 72: 706); rpp4 in PI 459025 (Hartwig R. R. (1986) Identification of a fourth major gene conferring to resistance to soybean rust. Crop Science, 26: 1135-1136) and rpp5 (Meyer J. D. F. (2009) Identification and analyses of candidate genes for Rpp4-mediated resistance to Asian Soybean Rust in soybean. Plant Physiol 150: 295-307). The resistance presented by each gene is limited to the specific pathogen variety and can be overcome in a short period of time due to the coevolution of host resistance and pathogen virulence. Even though there are soybean varieties that have superior traits, e. g. ASR tolerance, they are not fully resistant but still only tolerant to said disease.

Therefore, crop tolerance and activity against fungi do not always satisfy the needs of agricultural practice in many incidents and aspects. The use of new resistance sources are investigated with the focus lying on both: more effective fungicide application and identification and/or modification of genes which confer ASR tolerance/resistance.

WO 2010/049405 teaches a method for improving the health of a plant by the application of a combination containing a heteroaryl-substituted alanine compound and an agriculturally active compound such as for example the fungicides fluxapyroxad, bixafen, boscalid, isopyrazam or penthiopyrad. Therein, the improvement of the plant's health does not indicate a teaching for the control of ASR.

Furthermore, it has been previously reported by US 2010/0093715 that the application of a carboxamide fungicide to a transgenic plant resulted in a synergistic increase of plant health. Although it mentions a method for controlling ASR, the teaching is limited to plants with transgenic modifications. ASR tolerant transgenic plants are not described.

WO 2010/046380 describes a method of controlling pests and/or increasing the health of a plant by treating a cultivated plant with a carboxamide compound. Soybean varieties which are referred to in the description or the examples of this reference are transgenic plants. The soybean variety employed in the biological example of WO 2010/046380 contains a transgene conferring an herbicide tolerance. There is no hint in WO 2010/046380 that the application of a succinate dehydrogenase inhibitor (SDHI) fungicide to an ASR-tolerant, Stem canker resistant and/or Frog-eye leaf spot resistant conventionally bred soybean variety would result in a synergistic effect between the trait of said plant and the applied fungicide. Therefore, no sufficient teaching concerning the control over ASR on conventionally bred or transgenic ASR-tolerant, Stem canker resistant and/or Frog-eye leaf spot resistant soybean varieties is given.

General advantages of conventionally bred vs. transgenic plants include the following:

In many cases, traits introduced by conventional breading are more stable than traits introduced by transgenic methods. For conventionally bred plants, there is less risk of environmental contamination e.g. by horizontal gene transfer. In particular, for conventionally bred plants there is no risk that might be conferred by an antibiotic resistance gene that is routinely introduced in transgenic plants for selection purposes. Also, there is a strong economic advantage generated, as there is no need for expensive and longish deregulation proceedings in each country for conventionally bred plants.

Also the timespan and costs needed to develop a conventionally bred variety are much shorter than for transgenic varieties. In addition, in some countries the acceptance by the consumer is generally higher. Further, for conventionally bred plants there is no risk that beneficial plant properties are disturbed or even eliminated by the randomly occurring introduction of the transgene into the genome.

SUMMARY

Accordingly, it is an objective of the present invention to provide a method, which enables control over ASR on a conventionally bred ASR-tolerant, Stem canker resistant and/or Frog-eye leaf spot resistant soybean variety using a fungicide.

Furthermore, it is an objective of the present invention to provide a method, which enables control over ASR on a conventionally bred ASR-tolerant, Stem canker resistant and/or Frog-eye leaf spot resistant soybean variety using a fungicide, wherein there is a synergistic effect of the plant's traits and the fungicide.

Another objective of the present invention is to provide a method which enables control over ASR wherein the superior traits of a conventionally bred ASR-tolerant, Stem canker resistant and/or Frog-eye leaf spot resistant plant lead to a synergistic effect against ASR upon application of a fungicide.

Another objective of the present invention is to provide a method, which enables control over ASR on a conventionally bred ASR-tolerant, Stem canker resistant and/or Frog-eye leaf spot resistant soybean variety using a fungicide, wherein there is a synergistic effect of the plant's traits and the fungicide, and wherein there are additional advantages of using a conventionally bred as compared to a transgenic plant selected from the group consisting of higher stability of the new trait(s), less risk of environmental contamination, no risk of contamination by an antibiotic resistance gene, economic advantage, higher acceptance by the consumer, and no risk that beneficial plant properties are disturbed or even eliminated by the randomly occurring introduction of the transgene.

Surprisingly, it has been found that the use of a SDHI fungicide for treating ASR on a conventionally bred ASR-tolerant, Stem canker resistant and/or Frog-eye leaf spot resistant soybean variety displays a synergistic effect between the trait of said plant and the applied fungicide.

Synergistic in the present context means that the use of the SDHI fungicide in combination with the conventionally bred ASR-tolerant, Stem canker resistant and/or Frog-eye leaf spot resistant soybean variety exceeds the additive effect, to be expected on *Phakopsora pachyrhizi* and thus extends the range of action of the SDHI fungicide and of the active principle expressed by the conventionally bred ASR-tolerant, Stem canker resistant and/or Frog-eye leaf spot resistant soybean variety.

This surprising finding involves an inventive step over the prior art. E.g., as outlined above, the difference over WO 2010/046380 is not only that the biological example on soybean in WO 2010/046380 (page 139-140) pertains to a transgenic soybean variety as compared to a conventionally bred variety but also that the transgene of the soybean variety used in WO 2010/046380 confers herbicide tolerance (glyphosate), whereas the altered property of the conventionally bred variety claimed in the present invention pertains to ASR tolerance, Stem canker resistance and/or Frog-eye leaf spot resistance. It could not be expected that the treatment with the fungicide(s) according to the invention would result in a synergistic effect regarding the control of ASR between the trait of said plant and the applied fungicide.

Especially, it has been found that the application of at least one SDHI fungicide to a conventionally bred ASR-tolerant, Stem canker resistant and/or Frog-eye leaf spot resistant soybean variety leads to a synergistically enhanced action against *Phakopsora pachyrhizi* compared to the control rates that are possible with the same SDHI fungicide at wild type plants when applied to a conventionally bred ASR-tolerant, Stem canker resistant and/or Frog-eye leaf spot resistant soybean variety, parts of that plant, plant propagation material or at its locus of growth.

Accordingly, the present invention relates to a method for controlling ASR of a conventionally bred ASR-tolerant, Stem canker resistant and/or Frog-eye leaf spot resistant soybean variety comprising the application of a SDHI fungicide to said plant, plant propagation material, or at its locus of growth.

DETAILED DESCRIPTION OF A PREFERRED EMBODIMENT

According to a preferred embodiment of the present invention, the SDHI fungicide is applied at least at parts of the conventionally bred ASR-tolerant, Stem canker resistant and/or Frog-eye leaf spot resistant soybean variety, preferably the leaves, the roots, the flowers and/or the stem of the conventionally bred plant, and its seed.

SDHI Fungicides

In a preferred embodiment of the present invention it has been found that the application of at least one SDHI fungicide chosen from the group consisting of penflufen, isopyrazam, bixafen, sedaxane, fluxapyroxad, fluopyram, penthiopyrad, boscalid, N-[1-(2,4-dichlorophenyl)-1-methoxypropan-2-yl]-3-(difluoromethyl)-1-methyl-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(Dichlormethylen)-1,2,3,4-tetrahydro-1,4-methanonaphthalen-5-yl]-3-(difluormethyl)-1-methyl-1H-pyrazol-4-carboxamid, and N-[(1R,4S)-9-(Dichlormethylen)-1,2,3,4-tetrahydro-1,4-methanonaphthalen-5-yl]-3-(difluormethyl)-1-methyl-1H-pyrazol-4-carboxamid to a conventionally bred ASR-tolerant, Stem canker resistant and/or Frog-eye leaf spot resistant soybean variety leads to a synergistically enhanced action against *Phakopsora pachyrhizi* compared to the control rates that are possible with the same SDHI fungicide preferably chosen from the group consisting of the compounds as defined above at wild type plants when applied to a conventionally bred soybean variety, parts of that plant, plant propagation material or at its locus of growth.

According to a further preferred embodiment of the present invention, the at least one SDHI fungicide is chosen from the group consisting of penflufen, isopyrazam, bixafen, sedaxane, and fluxapyroxad.

Penflufen (chemical name: N-[2-(1,3-dimethylbutyl)phenyl]-5-fluor-1,3-dimethyl-1H-pyrazole-4-carboxamide) and methods for its production on basis of commercially available compounds can be found in WO 03/010149.

Isopyrazam is a mixture comprising both syn isomers of 3-(difluormethyl)-1-methyl-N-[(1RS,4SR,9RS)-1,2,3,4-tetrahydro-9-isopropyl-1,4-methanonaphthalen-5-yl]pyrazole-4-carboxamide and both anti isomers of 3-(difluormethyl)-1-methyl-N-[(1RS,4SR,9SR)-1,2,3,4-tetrahydro-9-isopropyl-1,4-methanonaphthalen-5-yl]pyrazole-4-carboxamide. Isopyrazam further comprises isopyrazam (anti-epimeric racemate 1RS,4SR,9SR), isopyrazam (anti-epimeric enantiomer 1R,4S,9S), isopyrazam (anti-epimeric enantiomer 1S,4R,9R), isopyrazam (syn epimeric racemate 1RS,4SR,9RS), isopyrazam (syn-epimeric enantiomer 1R,4S,9R), and isopyrazam (syn-epimeric enantiomer 1S,4R,9S). Isopyrazam and methods for its production on basis of commercially available compounds is given in WO 2004/035589.

Bixafen (chemical name: N-(3',4'-dichloro -5-fluoro-1,1'-biphenyl-2-yl)-3-(difluoromethyl)-1-methyl-1H-pyrazole-4-carboxamide) and methods of its production on basis of commercially available compounds can be found in WO 03/070705.

Sedaxane is a mixture comprising both cis isomers of 2'-[(1RS,2RS)-1,1' -bicycloprop-2-yl]-3-(difluoromethyl)-1-methylpyrazole-4-carboxanilide and both trans isomers of 2'-[(1RS,2SR)-1,1'-bicycloprop-2-yl]-3-(difluoromethyl)-1-methylpyrazole-4-carboxanilide. Sedaxane and methods for its production on basis of commercially available compounds can be found in WO 03/074491, WO 2006/015865 and WO 2006/015866.

Fluxapyroxad (chemical name: 3-(difluoromethyl)-1-methyl-N-(3',4',5'-trifluorobiphenyl-2-yl)-1H-pyrazole-4-carboxamide) and methods for its production on basis of commercially available compounds can be found in WO 2005/123690.

Fluopyram (chemical name: N-{[3-chloro-5-(trifluoromethyl)-2-pyridinyl]ethyl}-2,6-dichlorbenzamide and methods for its production on basis of commercially available compounds can be found in EP-A-1 531 673 and WO 2004/016088.

Penthiopyrad (chemical name: (RS)—N-[2-(1,3-dimethylbutyl9-3-thienyl]-1-methyl-3-(trifluoromethyl)-pyrazole-4-carboxamide) methods for its production on basis of commercially available compounds can be found in EP 0737682.

Boscalid (chemical name: 2-chloro-N-(4'-chlorobipheyl-2-yl)nicotinamide) and methods for its production on basis of commercially available compounds can be found in DE 19531813.

N-[1-(2,4-dichlorophenyl)-1-methoxypropan-2-yl]-3-(difluoromethyl)-1-methyl-1H-pyrazole-4-carboxamide is known from WO 2010/000612.

N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(Dichlormethylen)-1,2,3,4-tetrahydro-1,4-methanonaphthalen-5-yl]-3-(difluormethyl)-1-methyl-1H-pyrazol-4-carboxamid, and N-[(1R,4S)-9-(Dichlormethylen)-1,2,3,4-tetrahydro-1,4-methanonaphthalen-5-yl]-3-(difluormethyl)-1-methyl-1H-pyrazol-4-carboxamid are known from WO 2007/048556.

The above mentioned SDHI fungicides may be used alone or in combination with other active ingredients such as:

(The active ingredients specified herein by their "common name" are known and described, for example, in the Pesticide Manual ("The Pesticide Manual", 14th Ed., British Crop Protection Council 2006) or can be searched in the internet (e.g. http://www.alanwood.net/pesticides)).

Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl) cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy] phenyl}imidoformamide and O-[1-(4-methoxyphenoxy)-3,3-dimethylbutan-2-yl]1H-imidazole-1-carbothioate.

Inhibitors of the respiratory chain at complex I or II, for example carboxin, diflumetorim, fenfuram, flutolanil, furametpyr, furmecyclox, mepronil, oxycarboxin, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy) phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, and salts thereof.

Inhibitors of the respiratory chain at complex III, for example ametoctradin, amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyrametostrobin, pyraoxystrobin, pyribencarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl) ethanamide, (2E)-2-(methoxyimino)-N-methyl-2-{2-[(E)-({1-[3-(trifluoromethyl)phenyl]ethoxy}imino)methyl] phenyl}ethanamide, (2E)-2-{2-[({[(1E)-1-(3-{[(E)-1-fluoro-2-phenylethenyl]oxy}phenyl)ethylidene]amino}oxy) methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro -N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl] ethylidene}amino)oxy]methyl}phenyl)-2,4-dihydro-3H-1, 2,4-triazol-3-one, methyl (2E)-2-{2-[({cyclopropyl[(4-methoxyphenyl)imino]methyl}sulfanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl] phenyl}-2-methoxy-N-methylacetamide, (2R)-2-{2-[(2,5-dimethylphenoxy)methyl]phenyl}-2-methoxy-N-methylacetamide and salts thereof.

Inhibitors of the mitosis and cell division, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4] triazolo[1,5-a]pyrimidine, 3-chloro-5-(6-chloropyridin-3-yl)-6-methyl-4-(2,4,6-trifluorophenyl)pyridazine and salts thereof.

Compounds capable to have a multisite action, like for example bordeaux mixture, captafol, captan, chlorothalonil, copper hydroxide, copper naphthenate, copper oxide, copper oxychloride, copper(2+) sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations including calcium polysulphide, thiram, tolylfluanid, zineb, ziram, 2,6-dimethyl-1H,5H-[1,4]dithiino[2,3-c:5,6-c']dipyrrole-1,3,5,7 (2H,6H)-tetrone and salts thereof.

Compounds capable to induce a host defence, like for example acibenzolar-S-methyl, isotianil, probenazole, tiadinil and salts thereof.

Inhibitors of the amino acid and/or protein biosynthesis, for example andoprim, blasticidin-S, cyprodinil, kasugamycin, kasugamycin hydrochloride hydrate, mepanipyrim, pyrimethanil and salts thereof.

Inhibitors of the ATP production, for example fentin acetate, fentin chloride, fentin hydroxide and silthiofam.

Inhibitors of the cell wall synthesis, for example benthiavalicarb, dimethomorph, flumorph, iprovalicarb, mandipropamid, polyoxins, polyoxorim, validamycin A and valifenalate.

Inhibitors of the lipid and membrane synthesis, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

Inhibitors of the melanine biosynthesis, for example carpropamid, diclocymet, fenoxanil, phthalide, pyroquilon and tricyclazole.

Inhibitors of the nucleic acid synthesis, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

Inhibitors of the signal transduction, for example chlozolinate, fenpiclonil, fludioxonil, iprodione, procymidone, quinoxyfen and vinclozolin.

Compounds capable to act as an uncoupler, like for example binapacryl, dinocap, ferimzone, fluazinam and meptyldinocap.

Further compounds, like for example benthiazole, bethoxazin, capsimycin, carvone, chinomethionat, chlazafenone, cufraneb, cyflufenamid, cymoxanil, cyprosulfamide, dazomet, debacarb, dichlorophen, diclomezine, difenzoquat, difenzoquat methylsulphate, diphenylamine, ecomate, fenpyrazamine, flumetover, fluoroimide, flusulfamide, flutianil, fosetyl-aluminium, fosetyl-calcium, fosetyl-sodium, hexachlorobenzene, irumamycin, methasulfocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and salts, phenothrin, phosphorous acid and its salts, propamocarb-fosetylate, propanosine-sodium, proquinazid, pyrrolnitrine, tebufloquin, tecloftalam, tolnifanide, triazoxide, trichlamide, zarilamid, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl)pyridine, 2,3-dibutyl-6-chlorothieno[2,3-d]pyrimidin-4(3H)-one, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1, 3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulfonohydrazide, 5-methyl-6-octyl[1,2,4]triazolo[1,5-a]pyrimidin-7-amine, ethyl (2Z)-3-amino-2-cyano-3-phenylprop-2-enoate, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol and quinolin-8-ol sulfate (2:1).

Further compounds like for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole- 4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone and N-[2-(4-{[3-(4-chlorophenyl)prop-2-yn-1-yl]oxy}-3-methoxyphenyl)ethyl]-N2-(methylsulfonyl)valinamide.

Acetylcholinesterase (AChE) inhibitors, for example carbamates, e.g. Alanycarb, Aldicarb, Bendiocarb, Benfuracarb, Butocarboxim, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiodicarb, Thiofanox, Triazamate, Trimethacarb, XMC, and Xylylcarb; or organophosphates, e.g. Acephate, Azamethiphos, Azinphos-ethyl, Azinphos-methyl, Cadusafos, Chlorethoxyfos, Chlorfenvinphos, Chlormephos, Chlorpyrifos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fosthiazate, Heptenophos, Imicyafos, Isofenphos, Isopropyl O-(methoxyaminothio-phosphoryl)salicylate, Isoxathion, Malathion, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-methyl, Profenofos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Triclorfon, and Vamidothion.

GABA-gated chloride channel antagonists, for example cyclodiene organochlorines, e.g. Chlordane and Endosulfan; or phenylpyrazoles (fiproles), e.g. Ethiprole and Fipronil.

Sodium channel modulators/voltage-dependent sodium channel blockers, for example pyrethroids, e.g. Acrinathrin, Allethrin, d-cis-trans Allethrin, d-trans Allethrin, Bifenthrin, Bioallethrin, Bioallethrin S-cyclopentenyl isomer, Bioresmethrin, Cycloprothrin, Cyfluthrin, beta-Cyfluthrin, Cyhalothrin, lambda-Cyhalothrin, gamma-Cyhalothrin, Cypermethrin, alpha-Cypermethrin, beta-Cypermethrin, theta-Cypermethrin, zeta-Cypermethrin, Cyphenothrin [(1R)-trans isomers], Deltamethrin, Empenthrin [(EZ)-(1R) isomers), Esfenvalerate, Etofenprox, Fenpropathrin, Fenvalerate, Flucythrinate, Flumethrin, tau-Fluvalinate, Halfenprox, Imiprothrin, Kadethrin, Permethrin, Phenothrin [(1R)-trans isomer), Prallethrin, Pyrethrine (pyrethrum), Resmethrin, Silafluofen, Tefluthrin, Tetramethrin, Tetramethrin [(1R) isomers)], Tralomethrin, and Transfluthrin; or DDT; or Methoxychlor.

Nicotinic acetylcholine receptor (nAChR) agonists, for example neonicotinoids, e.g. Acetamiprid, Clothianidin, Dinotefuran, Imidacloprid, Nitenpyram, Thiacloprid, and Thiamethoxam; or Nicotine.

Nicotinic acetylcholine receptor (nAChR) allosteric activators, for example spinosyns, e.g. Spinetoram and Spinosad.

Chloride channel activators, for example avermectins/milbemycins, e.g. Abamectin, Emamectin benzoate, Lepimectin, and Milbemectin.

Juvenile hormone mimics, for example juvenile hormon analogues, e.g. Hydroprene, Kinoprene, and Methoprene; or Fenoxycarb; or Pyriproxyfen.

Miscellaneous non-specific (multi-site) inhibitors, for example alkyl halides, e.g. Methyl bromide and other alkyl halides; or Chloropicrin; or Sulfuryl fluoride; or Borax; or Tartar emetic.

Selective homopteran feeding blockers, e.g. Pymetrozine; or Flonicamid.

Mite growth inhibitors, e.g. Clofentezine, Hexythiazox, and Diflovidazin; or Etoxazole.

Microbial disruptors of insect midgut membranes, e.g. Bacillus thuringiensis subspecies israelensis, Bacillus sphaericus, Bacillus thuringiensis subspecies aizawai, Bacillus thuringiensis subspecies kurstaki, Bacillus thuringiensis subspecies tenebrionis, and BT crop proteins: Cry1Ab, Cry1Ac, Cry1Fa, Cry2Ab, mCry3A, Cry3Ab, Cry3Bb, Cry34/35Ab1.

Inhibitors of mitochondrial ATP synthase, for example Diafenthiuron; or organotin miticides, e.g. Azocyclotin, Cyhexatin, and Fenbutatin oxide; or Propargite; or Tetradifon.

Uncouplers of oxidative phoshorylation via disruption of the proton gradient, for example Chlorfenapyr, DNOC, and Sulfluramid.

Nicotinic acetylcholine receptor (nAChR) channel blockers, for example Bensultap, Cartap hydrochloride, Thiocyclam, and Thiosultap-sodium.

Inhibitors of chitin biosynthesis, type 0, for example Bistrifluron, Chlorfluazuron, Diflubenzuron, Flucycloxuron, Flufenoxuron, Hexaflumuron, Lufenuron, Novaluron, Noviflumuron, Teflubenzuron, and Triflumuron.

Inhibitors of chitin biosynthesis, type 1, for example Buprofezin.

Moulting disruptors, for example Cyromazine.

Ecdysone receptor agonists, for example Chromafenozide, Halofenozide, Methoxyfenozide, and Tebufenozide.

Octopamine receptor agonists, for example Amitraz.

Mitochondrial complex III electron transport inhibitors, for example Hydramethylnon; or Acequinocyl; or Fluacrypyrim.

Mitochondrial complex I electron transport inhibitors, for example METI acaricides, e.g. Fenazaquin, Fenpyroximate, Pyrimidifen, Pyridaben, Tebufenpyrad, and Tolfenpyrad; or Rotenone (Denis).

Voltage-dependent sodium channel blockers, e.g. Indoxacarb; or Metaflumizone.

Inhibitors of acetyl CoA carboxylase, for example tetronic and tetramic acid derivatives, e.g. Spirodiclofen, Spiromesifen, and Spirotetramat.

Mitochondrial complex IV electron transport inhibitors, for example phosphines, e.g. Aluminium phosphide, Calcium phosphide, Phosphine, and Zinc phosphide; or Cyanide.

Mitochondrial complex II electron transport inhibitors, for example Cyenopyrafen.

Ryanodine receptor modulators, for example diamides, e.g. Chlorantraniliprole and Flubendiamide.

Further active ingredients with unknown or uncertain mode of action, for example Amidoflumet, Azadirachtin, Benclothiaz, Benzoximate, Bifenazate, Bromopropylate, Chinomethionat, Cryolite, Cyantraniliprole (Cyazypyr), Cyflumetofen, Dicofol, Diflovidazin, Fluensulfone, Flufenerim, Flufiprole, Fluopyram, Fufenozide, Imidaclothiz, Iprodione, Pyridalyl, Pyrifluquinazon, and iodomethane; furthermore products based on Bacillus firmus (I-1582, BioNeem, Votivo) or one of the following known active compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934), 4-{[(6-bromopyridin-3-yl)methyl](2-fluoroethyl)amino}furan-2(5H)-one (known from WO2007/115644), 4-{[(6-fluoropyridin-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chlorpyridin-3-yl)methyl](2-fluoroethyl)amino}furan-2(5H)-one (known from WO2007/115644), 4-{[(6-chloropyridin-3-yl)methyl](2,2-difluoroethyl)amino}furan-2(5H)-one (known from WO2007/115644), 4-{[(6-chlor-5-fluoropyridin-3-yl)methyl](methyl)amino}furan-2 (5H)-one (known from WO2007/115643), 4-{[(5,6-dichloropyridin-3-yl)methyl](2-fluoroethyl)amino}furan-2(5H)-one (known from WO2007/115646), 4-{[(6-chloro-5-fluoropyridin-3-yl)methyl](cyclopropyl)amino}furan-2(5H)-one (known from WO2007/115643), 4-{[(6-chloropyridin-3-yl)methyl](cyclopropyl)amino}furan-2(5H)-one (known from EP-A-0 539 588), 4-{[(6-chlorpyridin-3-yl)methyl](methyl)amino}furan-2 (5H)-one (known from EP-A-0 539 588), {[1-(6-chloropyridin-3-yl)ethyl](methyl)oxido-λ4sulfanylidene} cyanamide (known from WO2007/149134) and its diastereomers {[(1R)-1-(6-chloropyridin-3-yl)ethyl](methyl)oxido-)λ4-sulfanylidene}cyanamide (A) and {[(1S)-1-(6-chloropyridin-3-yl)ethyl](methyl)oxido-λ4-sulfanylidene}cyanamide (B) (also known from WO2007/149134) as well as Sulfoxaflor (also known from WO2007/149134) and its diastereomers [(R)-methyl(oxido){(1R)-1-[6-(trifluoromethyl)pyridin-3-yl]ethyl}-λ4-sulfanylidene]cyanamide (A1) and [(S)-methyl(oxido){(1S)-1-[6-(trifluoromethyl)pyridin-3-yl]ethyl}-λ4-sulfanylidene]cyanamide (A2), referred to as group of diastereomers A (known from WO2010/074747, WO2010/074751), [(R)-methyl(oxido){(1S)-1-[6-(trifluoromethyl)pyridin-3-yl]ethyl}-λ4-sulfanylidene]cyanamide (B1) and [(S)-methyl(oxido){(1R)-1-[6-(trifluoromethyl)pyridin-3-yl]ethyl}-λ4-sulfanylidene]cyanamide (B2), referred to as group of diastereomers B (also known from WO2010/074747, WO2010/074751), and 11-(4-chloro-2,6-dimethylphenyl)-12-hydroxy-1,4-dioxa-9-azadispiro [4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluoroethyl)sulfinyl]phenyl}-3-(trifluoromethyl)-1H-1,2,4-triazol-5-amine (known from WO2006/043635), [(3 S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO2008/066153), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethylbenzenesulfonamide (known from WO2005/035486), 4-(difluoromethoxy)-N-ethyl-N-methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazol-2-amine (known from WO2008/104503), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280), 2-ethyl-7-methoxy-3-methyl-6-[(2,2,3,3-tetrafluoro-2,3-dihydro-1,4-benzodioxin-6-yl)oxy]quinolin-4-yl methyl carbonate (known from JP2008/110953), 2-ethyl-7-methoxy-3-methyl-6-[(2,2,3,3-tetrafluoro-2,3-dihydro-1,4-benzodioxin-6-yl)oxy]quinolin-4-yl acetate (known from JP2 00 8/1 10953), PF1364 (CAS-Reg.No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2 (5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO2010/005692), NNI-0711 (known from WO2002096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), (5RS,7RS; 5 RS,7 SR)-1-(6-chloro-3-pyridylmethyl)-1,2,3,5,6,7-hexahydro-7-methyl-8-nitro-5-propoxyimidazo[1,2-a]pyridine (known from WO2007/101369), 2-{6-[2-(5-fluoropyridin-3-yl)-1,3-thiazol-5-yl]pyridin-2-yl}pyrimidine (known from WO2010/006713), 2-{6-[2-(pyridin-3-yl)-1,3-thiazol-5-yl]pyridin-2-yl}pyrimidine (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO2010/069502), and (1E)-N-[(6-chloropyridin-3-yl)methyl]-N'-cyano-N-(2,2-difluoro-ethyl)ethanimidamide (known from WO2008/009360).

Conventionally Bred ASR-Tolerant, Stem Canker Resistant and/or Frog-Eye Leaf Spot Resistant Soybean Variety The conventionally bred ASR-tolerant, Stem canker resistant and/or Frog-eye leaf spot resistant soybean variety and its plant parts can be treated in accordance with the present invention. Plant parts are understood as meaning all aerial and subterranean parts and organs of the plants, such as shoot, leaf, flower and root, examples which may be mentioned being leaves, stems, flowers, fruiting bodies, and seeds, and also roots and rhizomes. The plant parts also include crop material and vegetative and generative propagation material, for example cuttings, rhizomes, slips and seeds. Preferably, plant parts are understood as meaning the leaves, the roots the flowers and/or the stem of the conventionally bred plant, and its seed. More preferably, plant parts are understood as meaning leaves.

The plants or plant varieties used according to the present invention are ASR-tolerant, Stem cranker resistant and/or Frog leaf spot resistant. Preferably, the ASR tolerance of the plant or plant varieties according to the present invention is conferred by a gene selected from the group consisting of Rpp1, Rpp2, Rpp3, Rpp4 and Rpp5 or a combination thereof. Most preferably, the ASR tolerance is conferred by a gene selected from the group consisting of Rpp2, Rpp4 and Rpp5 or a combination thereof.

The plants or plant varieties used according to the present invention are not transgenic. Transgenic organisms are produced by introducing an exogenous gene (a transgene) into a living organism using genetic engineering so that the organism will exhibit a new property. The genetic material of transgenic plants has been modified by the use of recombinant DNA techniques that under natural circumstances cannot readily be obtained by cross breeding, mutations or natural recombination, whereby the modification confers ASR-tolerance, Stem canker resistantance and/or Frog-eye leaf spot resistance or confers the increase of ASR-tolerance, Stem canker resistance and/or Frog-eye leaf spot resistance.

Genetic engineering is the direct human manipulation of an organism's genome using genetic transformation techniques. DNA sequences, whether from a different species or from the same species, which are inserted into the genome using transformation, are referred to herein collectively as "transgenes". A "transgene" also encompasses antisense, or sense and antisense sequences capable of gene silencing.

Numerous methods for plant transformation have been developed, including biological and physical plant transformation protocols (see, e.g., Glick, B. R. and Thompson, J. E. Eds. (CRC Press, Inc., Boca Raton (1993): 67-88 and Armstrong, "The First Decade of Maize Transformation: A Review and Future Perspective" Maydica 1999 (44):101-109). In addition, expression vectors and in vitro culture methods for plant cell or tissue transformation and regeneration of plants are available. See, e.g., Glick, B. R. and Thompson, J. E. Eds. (CRC Press, Inc., Boca Raton (1993): 89-119).

In contrast, non-transgenic plants are produced by traditional breeding techniques (e.g., crossing/backcrossing/selfing, etc.).

Preferably, the conventionally bred ASR-tolerant, Stem canker resistant and/or Frog-eye leaf spot resistant soybean variety according to the present invention is obtained upon conducting segregating generations, preferably the bulk Method, SSD (Single Seed Descent) and/or backcrossing.

More preferably, the conventionally bred ASR-tolerant, Stem canker resistant and/or Frog-eye leaf spot resistant soybean variety according to the present invention is obtained by the bulk method. In the bulk method, segregating generations, generally F2 and F5 are grown with the seeding and harvest of all the plants mixed in a single population. Therefore, in the bulk method, the seeds used for growing each segregating generation are a sample of the seeds harvested in the previous generation. After five generations of self-fertilizing crops, the plants exhibit a high degree of homozygosis and can be selected for individual harvest (Souza, A. P. Biologia Molecular Aplicada ao melhoramento. In: Recursos Genéticos e Melhoramento—Plantas. Luciano L. Nass; Alfonso C. C. Valois, Itamar S. de Melo; Maria Clêlia Valadres-Inglis. (Org.) 1ª Ed. Rononópolis, 2001, 1: 939-966).

In another embodiment the conventionally bred ASR-tolerant, Stem canker resistant and/or Frog-eye leaf spot resistant soybean variety according to the present invention is obtained by the SSD method. The SSD method was described by Brim in 1966 (Brim, C. A. ; 1966. A modified pedigree method of selection in soybeans. Crop Science, 6: 20) and consists of segregating generation advancement (from F2 to F5) harvesting a single pot (2 to 3 seeds) from each plant; however, only one plant from each pot is used to grow the next generation. A sample is harvested and conserved. In this way, at the end of the process, each line corresponds to a different F2 plant and, therefore, there is a reduction in the loss caused by deficient sampling or natural selection.

In another preferred embodiment the conventionally bred ASR-tolerant, Stem canker resistant and/or Frog-eye leaf spot resistant soybean variety according to the present invention is obtained by backcrossing. Backcrossing is not exactly a method for growing segregation populations. It is a strategy used to improve the phenotypic expression of a deficient trait, especially if this trait is of a qualitative inheritance. The use enables the transfer of a gene or of a few genes from a parent called donor parent (DP) to another parent called recurrent parent (RP), and the recurrent parent is usually a cultivar of commercial interest having some kind of deficiency in its cultivation that needs to be improved. This deficiency can be corrected by the process of transferring the gene from the donor parent, which does not have a deficiency, to the recurrent parent. This procedure, that is to say the cross of individuals from the segregating population with the recurring parent, is called backcrossing and is responsible for recovering almost 100% of the recurring parent genotype (Souza, A. P. Biologia Molecular Aplicada ao melhoramento. In: Recursos Genéticos e Melhoramento—Plantas. Luciano L. Nass; Alfonso C. C. Valois, Itamar S. de Melo; Maria Clêlia Valadres-Inglis. (Org.) 1ª Ed. Rononópolis, 2001, 1: 939-966).

Preferably, in the end of the selective processes as described above one or a few pure lines with superior traits that will originate a new cultivar are identified.

Most preferably, the plant varieties used according to the present invention are TMG 801 and/or TMG 803 from Tropical Melhoramento e Genética LTDA, Brasil.

The wild type soybean is preferably a plant, which has no superior trait as the conventionally bred ASR-tolerant, Stem canker resistant and/or Frog-eye leaf spot resistant soybean variety but is in any other property as similar as possible to a soybean, employed in the process of the present invention. The wild type plant is in its genome, transcriptome, proteome or metabolome as similar as possible to a plant, employed in the process of the present invention. Preferably, the wild type soybean is a Miyagishirome variety.

The treatment of the conventionally bred ASR-tolerant, Stem canker resistant and/or Frog-eye leaf spot resistant soybean varieties, its plant parts, plant propagation material, or at its locus of growth with the SDHI fungicide according to the present invention is carried out directly or by acting on the environment, habitat or storage space using customary treatment methods, for example by dipping, spraying, atomizing, misting, evaporating, dusting, fogging, scattering, foaming, painting on, spreading, injecting, drenching, trickle irrigation and, in the case of propagation material, in particular in the case of seed, furthermore by the dry seed treatment method, the wet seed treatment method, the slurry treatment method, by encrusting, by coating with one or more coats and the like. It is furthermore possible to apply the SDHI fungicide by the ultra-low volume method. Preferably, the SDHI fungicide is sprayed onto the soybean variety, parts of the plant, or its locus of growth.

The present invention further provides formulations and application forms prepared from the fungicidal compositions described above comprising at least one of the SDHI fungicides of the invention. The fungicidal formulations or application forms in question are preferably those which comprise auxiliaries, such as extenders, solvents and carriers, for example, and/or other auxiliaries, such as surface-active substances, for example.

Examples of customary formulations include solutions, emulsions, wettable powders, water-based and oil-based suspensions, water-based and oil-based suspension concentrates, powders, dusting products, pastes, soluble powders, granules, dispersible granules, soluble granules, granules for broadcasting, suspension-emulsion concentrates, natural materials impregnated with active compound, synthetic materials impregnated with active compound, fertilizers and ultra-fine encapsulations in polymeric compounds. Preferably, the application form prepared from the SDHI fungicide is an emulsion.

These formulations are produced in a conventional manner, for example by mixing of the active compounds with auxiliaries such as extenders, solvents and/or solid carriers, for example, and/or other auxiliaries such as surface-active substances, for example. The formulations are produced either in suitable equipment or else before or during application.

Auxiliaries used may be substances capable of giving the formulation of the SDHI fungicide, or the application forms prepared from these formulations (such as ready-to-use crop protection compositions, for example, such as spray liquors or seed dressings) particular properties, such as certain physical, technical and/or biological properties.

Examples of suitable extenders include water, polar and non-polar organic chemical liquids, such as those, for example, from the classes of aromatic and non-aromatic hydrocarbons (such as paraffins, alkylbenzenes, alkylnaphthalenes, chlorobenzenes), alcohols and polyols (which if desired may also be substituted, etherified and/or esterified), ketones (such as acetone, cyclohexanone), esters (including fats and oils) and (poly)ethers, simple and substituted amines, amides, lactams, (such as N-alkylpyrrolidones) and lactones, sulphones and sulphoxides (such as dimethyl sulphoxide).

Where water is utilized as an extender, organic solvents as well may be used as auxiliary solvents. Liquid solvents contemplated are essentially as follows: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, such as petroleum fractions, mineral and vegetable oils, alcohols, such as butanol or glycol and their ethers and esters, ketones, such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and water. Preferably, acetone is used as solvent.

In principle it is possible to use all suitable carriers. Carriers contemplated are more particularly the following: for example, ammonium salts and natural, finely ground minerals, such as kaolins, aluminas, talc, chalk, quartz, attapulgite, montmorillonite or diatomaceous earth, and synthetic, finely ground minerals, such as highly disperse silica, alumina and natural or synthetic silicates, resins, waxes and/or solid fertilizers. Mixtures of such carriers may likewise be used. Carriers contemplated for granules include the following: for example, crushed and fractionated natural minerals such as calcite, marble, pumice, sepiolite, dolomite, and also synthetic granules of finely ground organic and inorganic substances, and also granules of organic material such as sawdust, paper, coconut shells, maize cobs and tobacco stalks.

Liquefied gaseous extenders or solvents can also be used. Suitability is possessed more particularly by those extenders or carriers which are gaseous at standard temperature and under atmospheric pressure, examples being aerosol propellants, such as halogenated hydrocarbons, and also butane, propane, nitrogen and carbon dioxide.

Surface-active substances for the purposes of the invention are emulsifiers and/or foam formers, dispersants or wetting agents having ionic or nonionic properties, or mixtures of these surface-active substances. Examples thereof are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyltaurates), phosphoric esters of polyethoxylated alcohols or phenols, fatty acid esters of polyols, and derivatives of compounds comprising sulphates, sulphonates and phosphates, e.g. alkylaryl polyglycol ethers, alkylsulphonates, alkyl sulphates, arylsulphonates, protein hydrolysates, lignin-sulphite waste liquors and methylcellulose. The presence of a surface-active substance is advantageous if one of the SDHI fungicides and/or one of the inert carriers is insoluble in water and if application takes place in water. Preferably, polyoxyethylene alkly phenyl ether is used as an emulsifier.

Further auxiliaries present in the formulations and the application forms derived from them may include colorants, such as inorganic pigments, examples being iron oxide, titanium oxide and Prussian Blue, and organic dyes, such as alizarin dyes, azo dyes and metal phthalocyanine dyes, and nutrients, including trace nutrients, such as salts of iron, manganese, boron, copper, cobalt, molybdenum and zinc.

Additionally present may be stabilizers such as low-temperature stabilizers, preservatives, antioxidants, light stabilizers or other agents which enhance the chemical and/or physical stability. Additionally present may be foam formers or defoamers.

The formulations and application forms derived therefrom may further comprise, as additional auxiliaries, stickers such as carboxymethylcellulose, natural and synthetic polymers in powder, granule or latex form, such as gum arabic, polyvinyl alcohol, polyvinyl acetate, and also natural phospholipids, such as cephalins and lecithins, and synthetic phospholipids. Other possible auxiliaries include mineral and vegetable oils.

If desired there may also be further auxiliaries present in the formulations and in the application forms derived from them. Examples of such adjuvants include fragrances, protective colloids, binders, adhesives, thickeners, thixotropic agents, penetrants, retention promoters, stabilizers, sequestrants and complexing agents. Generally speaking, the active compounds may be combined with any solid or liquid adjuvant which is commonly used for formulation purposes.

The SDHI fungicide may be present in its commercially customary formulations and also in the application forms prepared from those formulations, in a mixture of other active compounds such as insecticides, attractants, sterilants, bactericides, acaricides, nematicides, fungicides, growth regulators, herbicides, safeners, fertilizers, semiochemicals or else agents for enhancing plant properties.

The formulations contain preferably between 0.00000001% and 98% by weight of the SDHI fungicide or, with particular preference, between 0.01% and 95% by weight of the SDHI fungicide, more preferably between 0.5% and 90% by weight, most preferably 1% by weight of the SDHI fungicide, based on the weight of the formulation. In the above context the term "SDHI fungicide" also includes combinations of SDHI fungicides.

Preferably, the formulations comprise at least one of the SDHI fungicides, a solvent, an emulsifier and/or water.

The SDHI fungicide content of the application forms (crop protection compositions) prepared from the formulations may vary within wide ranges. The SDHI fungicide concentration of the application forms may typically be between 0.002 ppm and 500 ppm of the SDHI fungicide, preferably between 0.2 ppm and 500 ppm, more preferably between 0.2 ppm and 100 ppm. In the above context, the term "SDHI fungicide" also includes combinations of SDHI fungicides.

Most preferably, penflufen is applied as an emulsion containing 0.2 ppm to 50 ppm of said fungicide.

Most preferably, isopyrazam is applied as an emulsion containing 0.2 ppm to 1 ppm of said fungicide.

Most preferably, bixafen is applied as an emulsion containing 0.2 ppm to 100 ppm of said fungicide.

Most preferably, sedaxane is applied as an emulsion containing 0.2 ppm to 25 ppm of said fungicide.

Most preferably, fluxapyroxad is applied as an emulsion containing 0.2 ppm to 25 ppm of said fungicide.

The application volume of the SDHI fungicide to a conventionally bred soybean variety, plant propagation material, or at its locus of growth is in the range of 0.01 kg/ha to 3 kg/ha, preferably 0.01 kg/ha to 1.5 kg/ha, more preferably 0.02 kg/ha to 0.5 kg/ha. Preferably the application volume of the SDHI fungicide is 25-500 l/ha, preferably 25-250 l/ha.

Preferably, the present invention is related to a kit of parts comprising a conventionally bred ASR-tolerant, Stem canker resistant and/or Frog-eye leaf spot resistant soybean variety and a SDHI fungicide selected from the group consisting of penflufen, isopyrazam, bixafen, sedaxane, fluxapyroxad, fluopyram, penthiopyrad, boscalid, N-[1-(2,4-dichlorophenyl)-1-methoxypropan-2-yl]-3-(difluoromethyl)-1-methyl-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(Dichlormethylen)-1,2,3,4-tetrahydro-1,4-methanonaphthalen-5-yl]-3-(difluormethyl)-1-methyl-1H-pyrazol-4-carboxamid, and N-[(1R,4S)-9-(Dichlormethylen)-1,2,3,4-tetrahydro-1,4-methanonaphthalen-5-yl]-3-(difluormethyl)-1-methyl-1H-pyrazol-4-carboxamid.

According to a further embodiment of the present invention, the kit of parts comprises a conventionally bred ASR-tolerant, Stem canker resistant and/or Frog-eye leaf spot resistant soybean variety and a SDHI fungicide selected from the group consisting of penflufen, isopyrazam, bixafen, sedaxane, and fluxapyroxad. According to a further embodiment of the present invention, the kit of parts comprises the conventionally bred ASR-tolerant, Stem canker resistant and/or Frog-eye leaf spot resistant soybean varieties TMG 801 and/or TMG 803.

Further preferred embodiments concerning this kit of parts comprise the embodiments as defined above.

The present invention also comprises a method for the production of an agricultural product comprising the application of a SDHI fungicide to a conventionally bred ASR-tolerant, Stem canker resistant and/or Frog-eye leaf spot resistant soybean variety, its plant propagation material, or at its locus of growth, and producing the agricultural product from said plant or parts of such a plant or plant propagation material.

According to a preferred embodiment of the present invention, the SDHI fungicide applied in said method for the production of an agricultural product is selected from the group consisting of penflufen, isopyrazam, bixafen, sedaxane, fluxapyroxad, fluopyram, penthiopyrad, boscalid, N-[1-(2,4-dichlorphenyl)-1-methoxypropan-2-yl]-3-(difluoromethyl)-1-methyl-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(Dichlormethylen)-1,2,3,4-tetrahydro-1,4-methanonaphthalen-5-yl]-3-(difluormethyl)-1-methyl-1H-pyrazol-4-carboxamid, and N-[(1R,4S)-9-(Dichlormethylen)-1,2,3,4-tetrahydro-1,4-methanonaphthalen-5-yl]-3-(difluormethyl)-1-methyl-1H-pyrazol-4-carboxamid.

According to a further preferred embodiment of the present invention, the SDHI fungicide applied in said method for the production of an agricultural product is applied at least at parts of the conventionally bred ASR-tolerant, Stem canker resistant and/or Frog-eye leaf spot resistant soybean variety, preferably the leaves, the roots, the flowers and/or the stem of the conventionally bred plant, and its seed. According to a further preferred embodiment the SDHI fungicide is applied as an emulsion, preferably containing 0.2 to 500 ppm of said fungicide. According to yet another preferred embodiment, the application volume of the SDHI fungicide is in the range of 0.01 to 3 kg/ha, preferably 0.01 to 1.5 kg/ha, more preferably 0.02 to 0.5 kg/ha. According to yet another preferred embodiment, the ASR tolerance in the conventionally bred ASR-tolerant, Stem canker resistant and/or Frog-eye leaf spot resistant soybean variety is conferred by the gene selected from the group consisting of Rpp1, Rpp2, Rpp3, Rpp4 and Rpp5 or a combination thereof. Even more preferably, the ASR tolerance is conferred by the gene selected from the group consisting of Rpp2, Rpp4 and Rpp5 or a combination thereof. Also preferably, the conventionally bred ASR-tolerant, Stem canker resistant and/or Frog-eye leaf spot resistant soybean variety is TMG 801 and/or TMG 803.

A further preferred embodiment of the present invention is also the use of a SDHI fungicide for controlling ASR of a conventionally bred ASR-tolerant, Stem canker resistant and/or Frog-eye leaf spot resistant soybean variety comprising the application of a SDHI fungicide to said plant, plant propagation material, or at its locus of growth.

EXAMPLE

One susceptible (Miyagishirome) and soybean varieties tolerant to soybean rust (*Phakospora pachyrhizi*) (TMG 801 and TMG 803) were cultivated in greenhouse up to 1.5-leaf stage. A suitable preparation of SDHI fungicide was produced by mixing 1 part per weight of the SDHI ingredient with 28.5 parts by weight of acetone as solvent and 1.5 parts by weight of polyoxyethylene alkyl phenyl ether as emulsifier. The concentrate was diluted with water to the desired concentrations.

Young plants of the susceptible and tolerant soybean varieties were sprayed with the preparation of the SDHI fungicide at the stated rate of application to evaluate the activity in controlling *Phakopsora pachyrhizi*.

One day after spraying, soybean plants were inoculated with an aqueous spore suspension of the causal agent of soybean rust (*Phakopsora pachyrhizi*). Plants were then placed in a greenhouse at approximately 20° C. and a relative atmospheric humidity of approximately 80%. The following trial schedule was applied:

Plants were evaluated 11 days after inoculation. The percentage of infected leaf area was determined visually. The results were calculated according to ABBOTT (% efficacy). 0% means an efficacy which corresponds to that of the control, while an efficacy of 100% means that no disease was observed.

The expected efficiencies for the SDHI fungicide and ASR-tolerant variety combinations were determined according to Colby's formula and compared to the observed efficiencies (Colby, S. R. (1967) Calculating synergistic and antagonistic responses of herbicide combinations, Weeds, 15: 20-22):

$$E = x + y - xy/100$$

Wherein E is the expected efficacy as a percent of the check when using the combination of a fungicide and ASR-tolerant variety; x is the efficacy of the percent check when using the fungicide; y is the efficacy of the percent check when using the ASR-tolerant variety.

By Comparison of the expected efficacy and the observed efficacy, the synergistic effect can be discerned. If the observed percent efficacy is higher than the calculated expected percent efficacy there is a synergistic effect.

TABLE 1

Penflufen

| Fungicide or tolerant variety | Application rate [ppm a.i.] | Efficacy [%] |
|---|---|---|
| (I) Penflufen | 50 | 60 |
|  | 25 | 55 |
|  | 10 | 20 |
|  | 5 | 20 |
|  | 1 | 0 |
|  | 0.2 | 0 |
| (II) soybean variety TMG 801 | — | 50 |
| (III) soybean variety TMG 803 | — | 50 |

TABLE 1-continued

Penflufen

Fungicide and tolerant variety combination

| | Application rate of penflufen [ppm a.i.] | Actual efficacy | Expected value, calculated using Colby's formula |
|---|---|---|---|
| (I) Penflufen + | 50 | 100 | 80 |
| (II) TMG 801 | 25 | 98 | 78 |
|  | 10 | 92 | 60 |
|  | 5 | 70 | 60 |
|  | 1 | 70 | 50 |
|  | 0.2 | 65 | 50 |
| (I) Penflufen + | 50 | 100 | 80 |
| (III) TMG 803 | 25 | 97 | 78 |
|  | 10 | 98 | 60 |
|  | 5 | 95 | 60 |
|  | 1 | 65 | 50 |
|  | 0.2 | 70 | 50 |

TABLE 2

Isopyrazam

| Fungicide or tolerant variety | Application rate [ppm a.i.] | Efficacy [%] |
|---|---|---|
| (I) Isopyrazam | 1 | 50 |
|  | 0.2 | 0 |
| (II) soybean variety TMG 803 | — | 30 |

Fungicide and tolerant variety combination

| | Application rate of isopyrazam [ppm a.i.] | Actual efficacy | Expected value, calculated using Colby's formula |
|---|---|---|---|
| (I) Isopyrazam + | 1 | 80 | 65 |
| (II) TMG 803 | 0.2 | 55 | 30 |

TABLE 3

Bixafen

| Fungicide or tolerant variety | Application rate [ppm a.i.] | Efficacy [%] |
|---|---|---|
| (I) Bixafen | 100 | 50 |
|  | 50 | 60 |
|  | 25 | 55 |
|  | 10 | 40 |
|  | 5 | 20 |
|  | 1 | 7 |
|  | 0.2 | 0 |
| (II) soybean variety TMG 803 | — | 55 |

Fungicide and tolerant variety combination

| | Application rate of bixafen [ppm a.i.] | Actual efficacy | Expected value, calculated using Colby's formula |
|---|---|---|---|
| (I) Bixafen + | 100 | 99 | 78 |
| (II) TMG 803 | 50 | 98 | 82 |
|  | 25 | 96 | 80 |
|  | 10 | 80 | 73 |
|  | 5 | 75 | 64 |
|  | 1 | 70 | 58 |
|  | 0.2 | 60 | 55 |

TABLE 4

Sedaxane

| Fungicide or tolerant variety | Application rate [ppm a.i.] | Efficacy [%] |
|---|---|---|
| (I) Sedaxane | 25 | 98 |
| | 10 | 70 |
| | 5 | 40 |
| | 1 | 0 |
| | 0.2 | 0 |
| (II) soybean variety TMG 801 | — | 65 |
| (III) soybean variety TMG 803 | — | 30 |

Fungicide and tolerant variety combination

| | Application rate of sedaxane [ppm a.i.] | Actual efficacy | Expected value, calculated using Colby's formula |
|---|---|---|---|
| (I) Sedaxane + | 25 | 99 | 99 |
| (II) TMG 801 | 10 | 98 | 90 |
| | 5 | 90 | 79 |
| | 1 | 82 | 65 |
| (I) Sedaxane + | 25 | 100 | 99 |
| (III) TMG 803 | 10 | 95 | 79 |
| | 5 | 75 | 58 |
| | 1 | 60 | 30 |
| | 0.2 | 50 | 30 |

TABLE 5

Fluxapyroxad

| Fungicide or tolerant variety | Application rate [ppm a.i.] | Efficacy [%] |
|---|---|---|
| (I) Fluxapyroxad | 25 | 98 |
| | 10 | 70 |
| | 5 | 60 |
| | 1 | 7 |
| | 0.2 | 0 |
| (II) soybean variety TMG 803 | — | 20 |

Fungicide and tolerant variety combination

| | Application rate of fluxapyroxad [ppm a.i.] | Actual efficacy | Expected value, calculated using Colby's formula |
|---|---|---|---|
| (I) Fluxapyroxad + | 25 | 97 | 98 |
| (III) TMG 803 | 10 | 80 | 76 |
| | 5 | 70 | 68 |
| | 1 | 65 | 26 |
| | 0.2 | 30 | 20 |

The results clearly demonstrate that the combination of a SDHI fungicide and a *Phakopsora pachyrhizi*-tolerant variety provides a synergistic effect with regard to the control of soybean rust. The observed activity of the SDHI fungicide and tolerant variety combination according to the invention was greater than the calculated activity using Colby's formula.

The most pronounced synergistic effect was found when applying fluxapyroxad with 1 ppm a. i. to TMG 803. The effect at low concentrations of said fungicide is more pronounced than the effect at concentrations up to 25 ppm a. i. The same tendency of the synergistic effect can be found for sedaxane which is applied to TMG 803. The application of this fungicide in lower concentrations (0.2 ppm a. i. to 1 ppm a. i.) provided a higher synergism than the application of sedaxane in concentrations of 5 ppm a. i. to 25 ppm a. i.

In contrast to this the application of bixafen to TMG 803 shows the highest synergistic effect for concentrations ranging from 100 ppm a. i. to 25 ppm a. i.

When applying penflufen with a concentration of 10 ppm a. i., the highest deviations of the actual efficacy from the expected value are obtained. This is irrespective of the plant type (TMG 801 or TMG 803).

Overall TMG 803 shows a higher potential for synergistic behavior irrespectively of the SDHI fungicide used.

The invention claimed is:

1. A method for controlling Asian soybean rust (ASR) of a conventionally bred ASR-tolerant, Stem canker resistant and/or Frog-eye leaf spot resistant soybean variety comprising applying a succinate dehydrogenase inhibitor (SDHI) fungicide to a plant, to plant propagation material, and/or at a locus of growth of said plant, wherein the conventionally bred ASR-tolerant, Stem canker resistant and/or Frog-eye leaf spot resistant soybean variety comprises TMG 801 and/or TMG 803.

2. The method according to claim 1, wherein the SDHI fungicide is selected from the group consisting of penflufen, isopyrazam, bixafen, sedaxane, fluxapyroxad, fluopyram, penthiopyrad, boscalid, N-[1-(2,4-dichlorphenyl)-1-methoxypropan-2-yl]-3-(difluoromethyl)-1-methyl-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S, 4R)-9-(Dichlormethylen)-1,2,3,4-tetrahydro-1,4-methanonaphthalen-5-yl]-3-(difluormethyl)-1-methyl-1H-pyrazol-4-carboxamid, and N-[(1R,4S)-9-(Dichlormethylen)-1,2,3,4-tetrahydro-1,4-methanonaphthalen-5-yl]-3-(difluormethyl)-1-methyl-1H-pyrazol-4-carboxamid.

3. The method according to claim 1, wherein the SDHI fungicide is applied at least to a part of the conventionally bred ASR-tolerant, Stem canker resistant and/or Frog-eye leaf spot resistant soybean variety.

4. The method according to claim 1, wherein ASR tolerance is conferred by at least one gene selected from the group consisting of Rpp1, Rpp2, Rpp3, Rpp4 and Rpp5.

5. The method according to claim 1, wherein ASR tolerance is conferred by at least one gene selected from the group consisting of Rpp2, Rpp4 and Rpp5.

6. A method according to claim 1, wherein the SDHI fungicide is applied as an emulsion.

7. A method according to claim 1, wherein application volume of the SDHI fungicide is in a range of from 0.01 to 3 kg/ha.

8. A kit of parts comprising a conventionally bred ASR-tolerant, Stem canker resistant and/or Frog-eye leaf spot resistant soybean variety and a SDHI fungicide selected from the group consisting of penflufen, isopyrazam, bixafen, sedaxane or fluxapyroxad, fluopyram, penthiopyrad, boscalid, N-[1(2,4-dichlorophenyl)-1-methoxypropan-2-yl]-3-(difluoromethyl)-1-methyl-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, N[(1S,4R)-9-(Dichlormethylen)-1,2,3,4-tetrahydro-1,4-methanonaphthalen-5-yl]-3-(difluormethyl)-1-methyl-1H-pyrazol-4-carboxamid, and N-[(1R,4S)-9-(Dichlormethylen)-1,2,3,4-tetrahydro-1,4-methanonaphthalen-5-yl]-3-(difluormethyl)-1-methyl-1H-pyrazol-4-carboxamid, wherein the conventionally bred ASR-tolerant, Stem canker resistant and/or Frog-eye leaf spot resistant soybean variety comprises TMG 801 and/or TMG 803.

9. A method for producing an agricultural product comprising applying a SDHI fungicide to a conventionally bred ASR-tolerant, Stem canker resistant and/or Frog-eye leaf spot resistant soybean variety, plant propagation material thereof, and/or at a locus of growth thereof, and producing said agricultural product from a plant and/or from parts of said plant and/or from plant propagation material, wherein the conventionally bred ASR-tolerant, Stem canker resistant and/or Frog-eye leaf spot resistant soybean variety comprises TMG 801 and/or TMG 803.

10. The method according to claim 9, wherein the SDHI fungicide is selected from the group consisting of penflufen, isopyrazam, bixafen, sedaxane, fluxapyroxad, fluopyram, penthiopyrad, boscalid, N-[1-(2,4-dichlorphenyl)-1-methoxypropan-2-yl]-3-(difluoromethyl)-1-methyl-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(Dichlormethylen)-1,2,3,4-tetrahydro-1,4-methanonaphthalen-5-yl]-3-(difluormethyl)-1-methyl-1H-pyrazol-4-carboxamid, and N-[(1R,4S)-9-(Dichlonnethylen)-1,2,3,4-tetrahydro-1,4-methanonaphthalen-5-yl]-3-(difluormethyl)-1-methyl-1H-pyrazol-4-carboxamid.

11. The method according to claim 1, wherein the SDHI fungicide comprises bixafen.

12. The method according to claim 1, wherein the SDHI fungicide comprises penflufen.

13. The method according to claim 1, wherein the SDHI fungicide comprises isopyrazam.

14. The method according to claim 1, wherein the SDHI fungicide comprises sedaxane.

15. The method according to claim 1, wherein the SDHI fungicide comprises fluxapyroxad.

16. The method according to claim 1, wherein the conventionally bred ASR-tolerant, Stem canker resistant and/or Frog-eye leaf spot resistant soybean variety comprises TMG 801.

17. The method according to claim 1, wherein the conventionally bred ASR-tolerant, Stem canker resistant and/or Frog-eye leaf spot resistant soybean variety comprises TMG 803.

18. The method according to claim 3, wherein the SDHI fungicide is applied at least to the leaves, the roots, the flowers and/or the stem of the conventionally bred plant, and/or to a seed of said plant.

19. The method according to claim 6, wherein the emulsion comprises from 0.2 to 500 ppm of said fungicide.

20. The method according to claim 1, wherein application volume of the SDHI fungicide is in a range of from 0.01 to 1.5 kg/ha.

21. A combination comprising a conventionally bred ASR-tolerant, Stem canker resistant and/or Frog-eye leaf spot resistant soybean variety and a succinate dehydrogenase inhibitor (SDHI) fungicide, wherein the conventionally bred ASR-tolerant, Stem canker resistant and/or Frog-eye leaf spot resistant soybean variety comprises TMG 801 and/or TMG 803.

* * * * *